United States Patent [19]
Rometsch

[11] Patent Number: 5,632,278
[45] Date of Patent: May 27, 1997

[54] DEVICE FOR AUTOMATICALLY MEASURING THE BLOOD PRESSURE

[75] Inventor: Rainer Rometsch, Wildberg, Germany

[73] Assignee: Hewlett-Packard Company, Palo Alto, Calif.

[21] Appl. No.: 680,972

[22] Filed: Jul. 16, 1996

Related U.S. Application Data

[63] Continuation of Ser. No. 288,662, Aug. 9, 1994, abandoned.

[30] Foreign Application Priority Data

Sep. 16, 1993 [DE] Germany ............... 43 31 450.3

[51] Int. Cl.$^6$ ........................................ A61B 5/02
[52] U.S. Cl. .................... 128/672; 128/680; 128/685
[58] Field of Search ....................... 128/672, 677–682, 128/685–686

[56] References Cited

U.S. PATENT DOCUMENTS

| | | |
|---|---|---|
| 4,037,587 | 7/1977 | Kaneda et al. . |
| 4,116,230 | 9/1978 | Gorelick . |
| 4,146,018 | 3/1979 | Aldridge et al. . |
| 4,369,951 | 1/1983 | Marsoner et al. . |
| 4,459,991 | 7/1984 | Hatschek . |
| 4,627,440 | 12/1986 | Ramsey, III et al. . |
| 4,969,466 | 11/1990 | Brooks . |

FOREIGN PATENT DOCUMENTS

| | | |
|---|---|---|
| 0014977A1 | 9/1980 | European Pat. Off. . |
| 0053228B1 | 6/1982 | European Pat. Off. . |
| 0208520B1 | 1/1987 | European Pat. Off. . |
| 0297146B1 | 1/1989 | European Pat. Off. . |
| 0333332A1 | 9/1989 | European Pat. Off. . |
| 0335179B1 | 10/1989 | European Pat. Off. . |
| 2251308C3 | 5/1973 | Germany . |
| 2902356A1 | 7/1980 | Germany . |
| 2917254A1 | 10/1980 | Germany . |
| 3130271A1 | 2/1983 | Germany . |
| 3424535A1 | 1/1986 | Germany . |
| 3605667C2 | 9/1986 | Germany . |
| 3536556A1 | 4/1987 | Germany . |
| 3916395A1 | 11/1989 | Germany . |
| WO88/00297 | 1/1988 | WIPO . |

*Primary Examiner*—Angela D. Sykes
*Assistant Examiner*—Ryan Carter

[57] ABSTRACT

A blood pressure measuring device comprises a sphygmomanometer cuff, a pressure generation device, a pressure sensor, a valve for controllably venting the cuff, and a control unit for controlling the valve. In order to achieve, using only one single valve, a precise adjustment of the cuff pressure of sleeves having different volumes, the valve is constructed as a squeezed tube valve and comprises an elastic tube and a squeezing device adapted to be actuated by an electromagnet and used for said elastic tube, said magnet having a structural design of such a nature that the gradient of the force with respect to the displacement of its force/displacement characteristic is at each operating point smaller than that of the force/displacement characteristic of the elastic tube.

10 Claims, 3 Drawing Sheets

DEVICE FOR AUTOMATICALLY MEASURING THE BLOOD PRESSURE

This application is a continuation of application Ser. No. 08/288,662 filed Aug. 9, 1994, now abandoned.

FIELD OF THE INVENTION

The present invention refers to a device for automatically measuring the blood pressure, comprising a sphygmomanometer cuff, a pressure generation device for filling the cuff, a pressure sensor for detecting the cuff pressure, a valve for controllably venting the cuff, and a control unit for controlling the valve.

DESCRIPTION OF THE PRIOR ART

For non-invasive measurement of the blood pressure, the blood pressure is measured either manually or automatically.

When the blood pressure is measured manually, an opening provided in a pneumatic system and defining a discharge valve is opened to a greater or lesser extent via a hand-operated mechanism, whereby the discharge rate of a cuff, which was previously pumped up to a specific starting pressure, can be adjusted by hand.

DE-2251308A discloses the use of a cam disk for manually adjusting the discharge valve opening, said cam disk defining an actuating stop so as to fix predetermined discharge rates.

EP-0014977A discloses the measure of coupling the cuff pressure of a manual blood pressure measuring device via a diaphragm to a tappet, which, depending on the instantaneous cuff pressure, opens a wedge-shaped aperture to a greater or lesser extent, whereby a discharge rate which is essentially pressure-independent with respect to time is to be achieved.

US-4146018A discloses that, in a blood pressure measuring system of the above-mentioned type, the discharge rate is controlled by deforming the external shape of a tube, said external shape of the tube defining together with an internal structure of a housing a gaplike aperture.

US-4037587 discloses that a manual blood pressure measuring system of the above-mentioned type includes a valve, which is defined by a deformable O-ring and a bolt, which, in its position of rest, is centrally arranged within said O-ring. By forcing the bolt out of its central position within the O-ring, a controllable gap is opened through which the air can escape.

DE-3536556A shows a manual blood pressure measuring system in which the discharge valve is defined by a tube-shaped, elastic member, which is adapted to be raised from a pierced tappet by compression and which thus opens an air passage opening.

In such manual blood pressure measuring devices, the valve is a valve of the "normally closed type", which permits a reduction of the cuff pressure only during its actuation.

Furthermore, it is common practice that, in such known manual blood pressure measuring devices, a lock-in position for the discharge valve is provided, said lock-in position permitting maximum opening of the valve for the purpose of rapid venting of the cuff.

More recently, however, the blood pressure measuring devices used are predominantly automatic blood pressure measuring devices. The structural design of such an automatic blood pressure measuring device is shown in FIG. 1.

A simple embodiment of the known automatic blood pressure measuring device shown in FIG. 1 comprises a sphygmomanometer cuff 1, which is wrapped around the patient's arm, for example, a pressure generation device 2, which can be defined by a diaphragm pump and which serves to fill the cuff 1, a pressure sensor 3 for detecting the cuff pressure, a discharge valve 4 used for controllably venting the cuff 1, as well as a control unit 5 constructed such that it is adapted to control the pressure generation device 2 and the valve 4 as well as to acquire the measured values supplied by the pressure sensor 3.

In a manner known per se, the pressure sensor 3 can serve to detect the oscillations, when the oscillometric measurement method is used. When a measurement according to Korotkov is carried out, this function can be realized by a microphone in the cuff 1.

The cuff 1, the pressure generation device 2, the pressure sensor 3 as well as the valve 4 are interconnected via a system of flexible tubes 8.

Such automatic blood pressure measuring devices use two different methods for controlling the valve 4 used for venting the cuff 1. These two methods are stepwise venting on the one hand and continuous venting on the other.

In such devices for automatically measuring the blood pressure, different sphygmomanometer cuffs 1 are used, viz. cuffs used for neonates and having a small volume of a view ccm, cuffs having a medium volume which are wrapped around the patient's arm and cuffs having a large volume of several 100 ccm which are wrapped around the patient's leg.

In the known automatic blood pressure measuring devices, ordinary directional control valves having two switching states, viz. open and closed, are normally used as valves for controllably venting the cuff.

These directional control valves have a fixed venting characteristic, which causes the discharge rate to decrease as the cuff pressure decreases, and this will result in a venting curve having the shape of an exponential function.

These directional control valves are normally commercially available valves in which the flowing medium can directly come into contact with the valve materials. The flowing medium is normally air, which can contain contaminations, such as dust, cleansing agent residues and the like. The valve materials frequently include corrosive materials, such as non-noble metals.

It is also known to use valves for continuous venting in automatic blood pressure measuring devices, said valves having low discharge rates, since they are open during the whole discharge process. When stepwise venting is carried out, valves with high discharge rates are used so that the discharge times, which constitute part of the overall measurement time, are kept short.

As will be explained hereinbelow, specific problems arise in connection with the method of stepwise venting of the sphygmomanometer cuff on the one hand and in connection with the method of continuous venting of the sphygmomanometer cuff on the other.

Problems arising when blood pressure measuring devices of the continuous-venting type are used:
due to the fact that the venting curve has a shape resembling an exponential function, a linear decrease of pressure is impossible, and this will result in extensions of the measurement time when measurements in the lower pressure ranges are carried out. Such blood pressure measuring devices permit neither a purposeful, rapid passage through a pressure range nor rapid discharge of the residual pressure when the measurement has been finished.

In connection with different cuff sizes, i.e. when sphygmomanometer cuffs with different volumina are used for the blood pressure measuring device, venting curves having different degrees of steepness will be obtained, the gradient of the venting curve being given by the time constant resulting from the cuff volume and the flow resistance of the valve. In view of the fact that the venting rates must not exceed predetermined limits so as to permit precise measuring of the blood pressure, the field of application is strongly limited. This means that a specific blood pressure measuring device is, for example, only suitable for measuring the blood pressure of adults using very specific cuff sizes.

In the prior art, attempts have already been made to these problems by means of various measures. Typical solution concepts are the following ones:

the use of two or more valves having, if necessary, different nominal widths for realizing different discharge behaviours by successive or parallel operation of the valves. PCT/FR88-00297, for example, discloses the use of three valves.

Normally, two valves are used, one being a quick-discharge valve and the other one being a precision-discharge valve. In this respect, reference is made to DE-3424535A, EP-0335179A, EP-0297146A and DE-3605667A.

EP-0333332A discloses the use of a valve with three switching states for discharge control; by means of said valve, two different discharge openings having different cross-sections can be switched.

The use of pulse-width modulated valve control means. In such systems, which are known e.g. from DE-3916395A, EP-0053228A and US-4116230A, a change in the discharge rate is achieved by varying the pulse duty ratio of the valve control signal. In other words, the ratio of valve opening to valve closing times is changed for varying the discharge characteristic. This method, however, necessitates the use of very fast valves.

The use of a valve having an adjustable discharge characteristic. DE-3130271, for example, shows a valve defined by a valve seat and a slender cone, which is guided via a suitable gearing by means of an electromotor or a stepping motor. The driving technique used results in high response times of the valve.

Problems arising when blood pressure measuring devices of the stepwise-venting type are used:

due to the above-described shape of the venting curve resembling an exponential function, the opening times of the valves must be changed for obtaining, as required in connection with oscillometric measurements, the desired pressure steps at each pressure level. With decreasing cuff pressures, this will result in longer opening times and, consequently, in longer measurement times. Moreover, it may happen that, under unvafourable conditions, such as high cardiac frequencies and long venting times, some oscillations can no longer be used.

For solving this problem, the prior art discloses the measure of using valves with high discharge rates so that the valve opening times and the venting times are kept within tolerable limits even in connection with small cuff pressures. However, this solution concept causes an additional problem.

If the discharge rate is dimensioned such that it is adapted e.g. to large cuffs (cuffs which are to be wrapped around the arm or the leg of an adult), the opening time will have to be reduced for smaller cuffs so as to realize the desired pressure steps. This means that high requirements will have to be met by the response times and the switching speed of the valves.

Since, as has been mentioned hereinbefore, the cuff volumes may range from a few ccm to several 100 ccm in connection with cuffs for neonates and cuffs which are to be wrapped around an adult's leg, a single valve can only cover a subrange due to its response times.

Commercially available directional control valves having a sufficient response time are, in most cases, complicated and composed of a large number of parts so that they cannot be realized at a reasonable price.

This problem has already been recognized in US-4627440A. A solution possibility of this probelm is explained in EP-0208520 in the manner following hereinbelow. Just as the continuous venting method which has already been described, the solution possibility in question uses two valves having different or identical discharge rates or one valve having an adjustable discharge opening, switching over to a different valve having a higher discharge rate being effected or an additional valve being connected to the system, if the discharge rate rises to a predetermined value of e.g. 8 ms/mmHg due to a decreasing cuff pressure. Also the adjustable variant mentioned hereinbefore is described as valve with two or more opening widths.

DE-2902356 already discloses the use of a squeezed tube valve for changing the direction of or shutting off a stream of gas or liquid, said squeezed tube valve being actuated by a rotatable lever with a roller, which is driven e.g. by a synchronous motor. This valve is comparatively slow and requires a comparatively high expenditure of technical means for electric control.

It is also known to use in the field of medical engineering squeezed tube valves for respiratory gas supervision for closed-loop control of a flow of gas in respirators.

SUMMARY OF THE INVENTION

It is an object of the present invention to further develop a device for automatically measuring the blood pressure of the type mentioned at the beginning in such a way that a simple and precise adjustment of the cuff pressure will be achieved even in cases in which different cuffs with different volumes are used.

This object is achieved by a device for automatically measuring the blood pressure comprising a sphygmomanometer cuff, a pressure generation device for filling the cuff, a pressure sensor for detecting the cuff pressure, a valve for controllably venting the cuff, said valve comprising an elastic tube and a squeezing device adapted to be actuated by an electromagnet and used for said elastic tube, and a control unit for controlling the valve, wherein said electromagnet has a structural design of such a nature that the gradient of the force with respect to the displacement of its force/displacement characteristic is at each operating point smaller than the gradient of the force with respect to the displacement of the force/displacement characteristic occurring when the elastic tube is squeezed.

In a preferred embodiment of the invention, the electromagnet has a structural design of such a nature that, with a given drive current, the force of said electromagnet is essentially independent of the actuating displacement.

In a further preferred embodiment of the invention, the squeezing device comprises a bearing device, which is arranged on one side of the tube, and a tappet actuated by the electromagnet and arranged in such a way that is adapted to be pressed onto the tube on the side of the tube located opposite the bearing device so as to squeeze the tube between the bearing device and the tappet.

In a further preferred embodiment of the invention, the bearing device is provided with a convex contact surface for the tube, and the tappet is provided with a flat contact surface for the tube.

In another preferred embodiment of the invention, the bearing device is provided with a flat contact surface for the tube, and the tappet is provided with a convex contact surface for the tube.

In another preferred embodiment of the invention, when the cuff is being filled, the control unit holds the valve in a partly open condition so as to cause a retarded pressure rise of the cuff pressure during the cuff-filling operation.

The invention is based on the finding that the above-described problems concerning the strongly limited field of use of known blood pressure measuring devices for specific cuff sizes as well as the problem of undesirably long measurement times can be eliminated by providing a valve which comprises an elastic tube and a squeezing device adapted to be actuated by an electromagnet and used for said elastic tube, the present invention teaching that the electromagnet should have a structural design of such a nature that the gradient of the force with respect to the displacement of its force/displacement characteristic is at each operating point of the valve smaller than the gradient of the force with respect to the displacement of the force/displacement characteristic occurring when the elastic tube is squeezed.

In other words, the present invention recognizes that the squeezed tube valve, which, up to now, has predominantly been used for unproblematic control tasks in the prior art, can be used as a valve for an automatic blood pressure measuring device according to the generic clause provided that the force/displacement characteristic of the electromagnet used is adapted in the manner described hereinbefore to the force/displacement characteristic occurring when the elastic tube is squeezed transversely to its longitudinal dimension. The valve according to the present invention prevents the non-linear operating behaviour of known squeezed tube valves which shows a break point; when said known squeezed tube valves are used, the increasing squeezing force will result in a non-linear, instable state in which the tube will collapse and thus be squeezed off abruptly.

In other words, the invention recognizes that an essentially continuous connection between the passage cross-section of the tube and the actuating or drive current of the electromagnet can be achieved, when the characteristic of the electromagnet used is adapted, in accordance with the present invention, to the properties of the elastic tube used.

By using a valve, which comprises a tube and a squeezing device adapted to be actuated by an electromagnet, in accordance with the present invention, the air discharged from the cuff as well as possible contaminations will be prevented from coming into contact with additional valve components. The tube is deformed and subject to milling, when the valve is actuated, so that a self-cleaning effect will be produced. Due to the elasticity of the tube, the valve according to the present invention does not require the use of a readjusting spring.

The blood pressure measuring device according to the present invention permits the use of cuffs with different volumes, since the control of the venting process can be achieved by means of only one single valve for all cuff sizes, without any undesirably long measurement times being caused. The valve according to the present invention can be actuated in a continuous as well as in a stepwise mode so that the blood pressure measuring device according to the present invention can be controlled by any desired control algorithm.

In accordance with a preferred embodiment of the present invention, the control unit holds the valve in a partly open condition during the cuff-filling operation so as to cause a retarded pressure rise of the cuff pressure. The pressure generation devices of such blood pressure measuring devices are typically designed such that the inflation time will amount to approx. 6 seconds when normal cuff sizes are used. If a cuff having a very small volume is used in connection with such a blood pressure measuring device, this will result in a very rapid pressure rise when the cuff is being inflated so that, in most cases, it will be impossible to adjust the desired pressure value at the first attempt. Due to the fact that, in accordance with the present invention, the valve is controlled during the cuff-filling operation in such a way that it is held in a partly open condition, said valve fulfills a bypass-like function with the aid of which part of the inflation volume can be discharged into the atmosphere in cases in which cuffs having a small volume are used. A predetermined pressure rise time can thus also be achieved in connection with cuffs having a small volume.

BRIEF SHORT DESCRIPTION OF THE DRAWINGS

In the following, preferred embodiments of the present invention will be explained in detail with reference to the drawings enclosed, in which.

Figure 4:
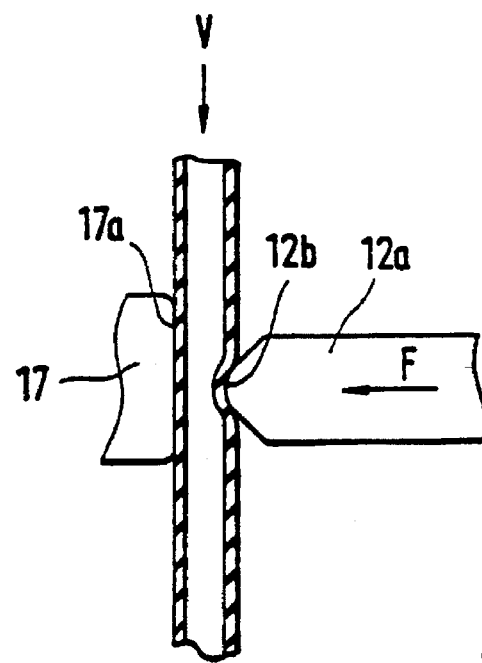
Figure 5:
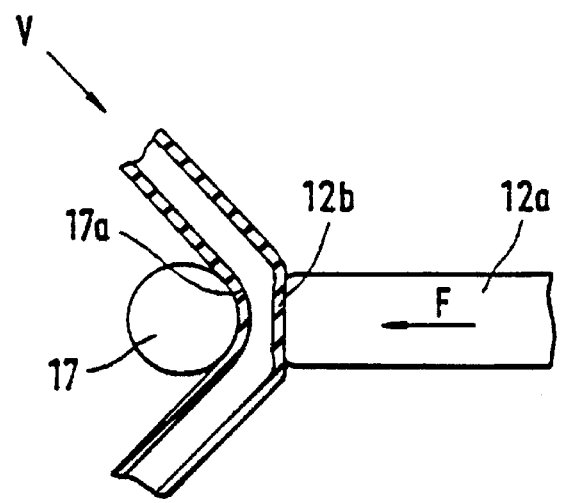
Figure 6:
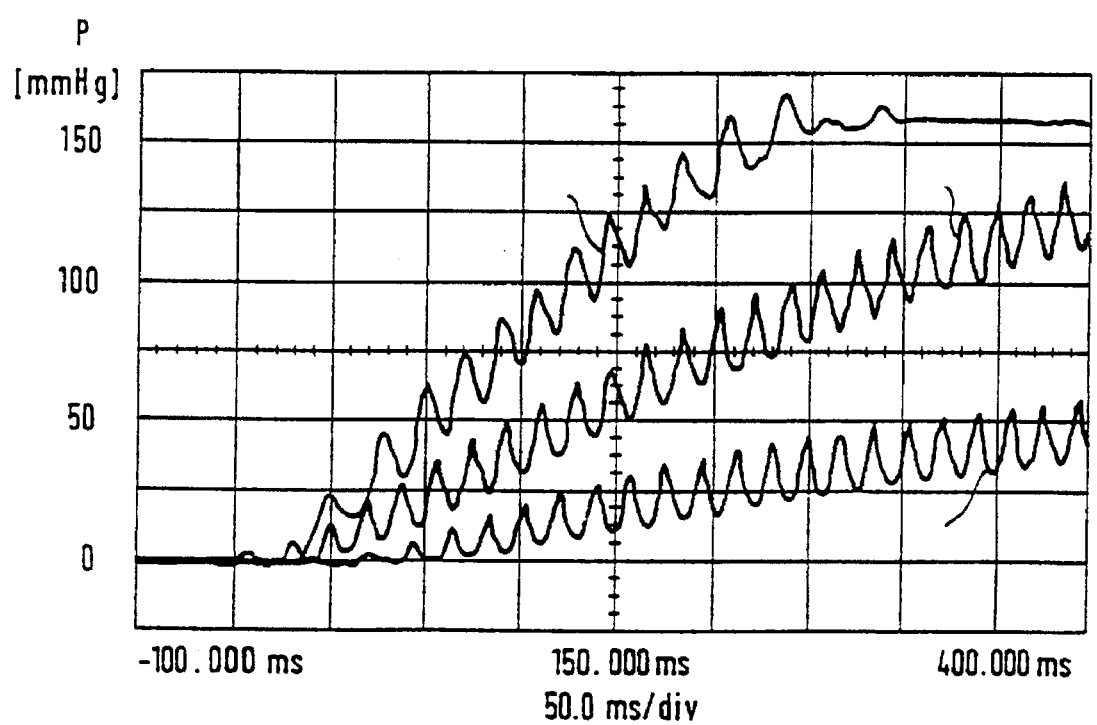

FIG. 4 and 5 are drawings of alternative embodiments of a squeezing device for the valve of the blood pressure measuring device according to the present invention; and FIG. 6 includes time-dependent pressure characteristic curves occurring during the cuff-inflation process when the valve of the blood pressure measuring device according to the invention is operated in a bypass-like mode of operation.

DESCRIPTION OF PREFERRED EMBODIMENTS OF THE INVENTION

Figure 1:
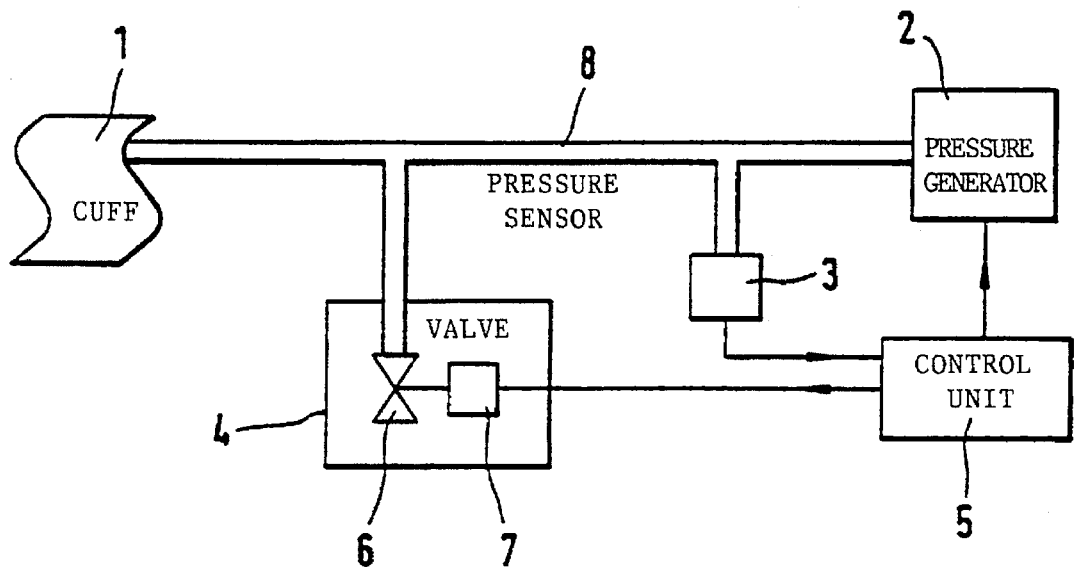
FIG. 1 is a diagram of the structure of a known automatic blood pressure measuring device.
Figure 2:
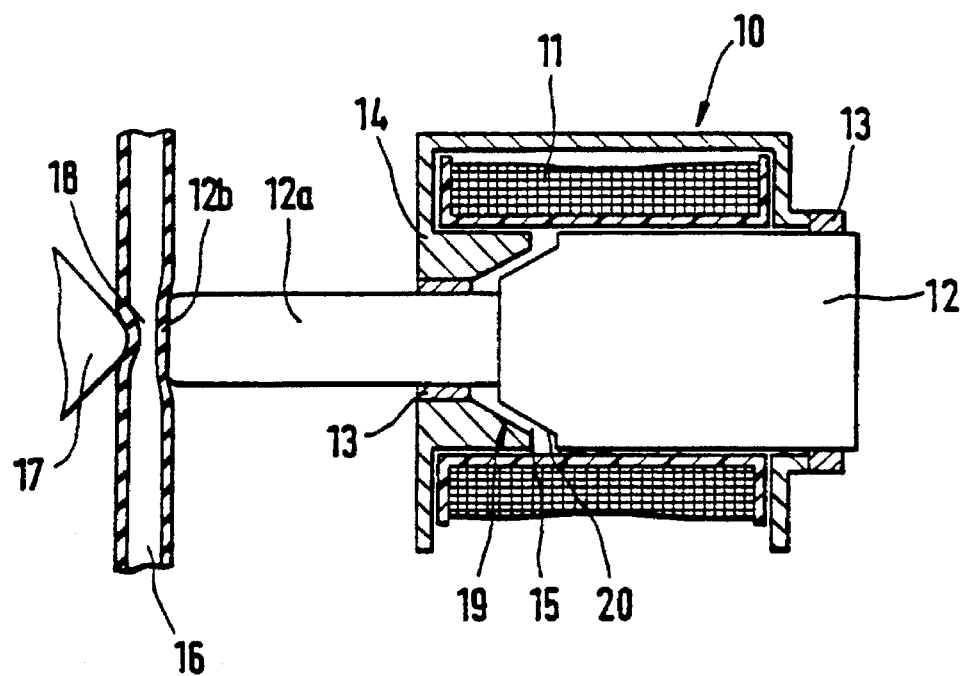
FIG. 2 is a a cross-sectional representation of an embodiment of the valve used in the blood pressure measuring device according to the present invention.

The basic structure of the blood pressure measuring device according to the present invention corresponds to the structure of the blood pressure measuring device according to the prior art shown in FIG. 1, the present invention teaching that the valve 4 is implemented, in the manner shown in FIG. 2 by way of example, by an elastic tube 16 and a squeezing device 12a, 17, which is adapted to be actuated by an electromagnet 10.

As will be explained in detail hereinbelow, the structural design of the electromagnet 10 is, according to the present invention, of such a nature that the gradient of the force with respect to the displacement of its force/displacement characteristic is at each operating point smaller than the gradient of the force with respect to the displacement of the force/displacement characteristic occurring when the elastic tube 16 is squeezed.

As can be seen in detail in FIG. 2, the electromagnet, designated generally by reference numeral 10 in said figure, comprises a winding 11, a movable armature 12, a non-magnetic tappet 12a connected to said armature 12, said components 12, 12a being guided by two support members 13. Both support members 13 are connected to a yoke 14. The yoke 14 defines the pole surfaces and part of the magnetic circuit. An air gap 15 is provided between the yoke 14 and the armature 12. Upon excitation of the winding 11 by a current, a magnetic field will be created within the air gap 15, said magnetic field drawing the armature 12 against the yoke 14 so that the tappet 12a will be pressed onto one side of the tube 16 with its front contact surface 12b, the opposite side of said tube 16 being thus pressed onto a bearing device 17.

The magnitude of the magnetic force and, consequently, of the squeezing force acting on the tube 16 depends on the magnitude of the current as well as on the geometry of the air gap 15.

Figure 3:
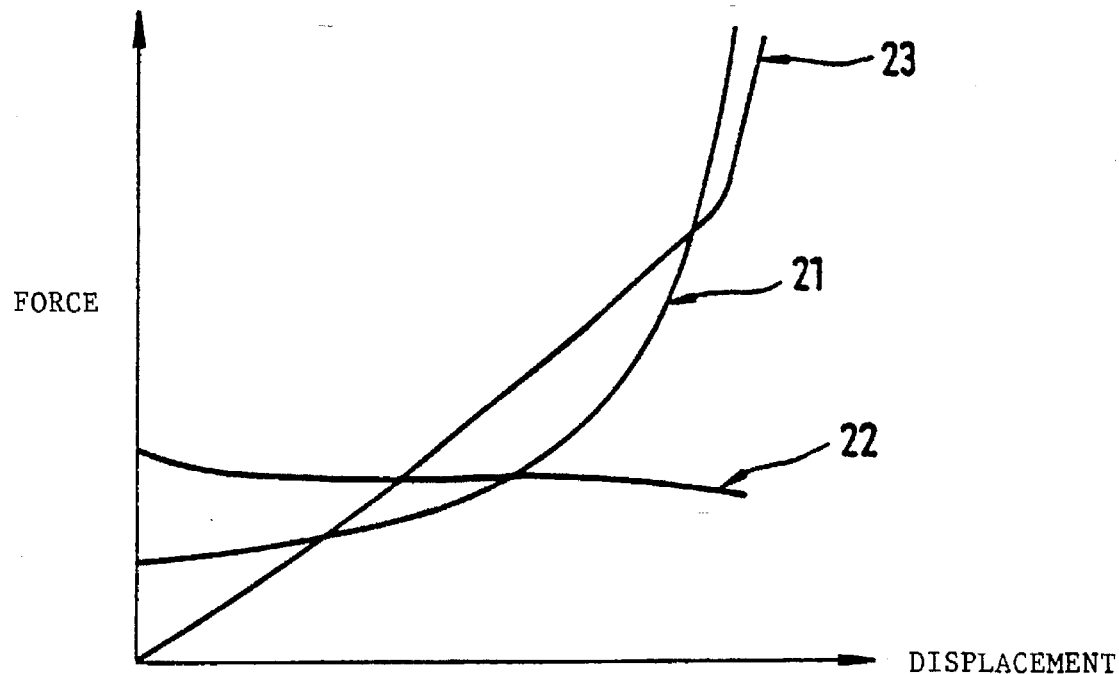
FIG. 3 is a representation of different force/displacement characteristics for two electromagnets as well as for the squeezing of an elastic tube.

As will be explained hereinbelow with reference to FIG. 3, the present invention adapts, by providing the electromagnet 10 with an appropriate structural design, the force/displacement characteristic of said electromagnet to the force/displacement characteristic occurring when the elastic tube is squeezed. The curve 21 shown in FIG. 3 shows the shape of the force/displacement characteristic of a normal magnet. This shape of the force/displacement characteristic of the normal magnet shows a gradient of the force with respect to the displacement which becomes steeper and steeper as the actuating displacement increases, i.e. as the size of the air gap decreases. The figure also shows as curve 23 the shape of the force/displacement characteristic of an elastic tube, the shape of the curve on the other side of the break point being representative of the range in which the tube is closed almost completely. The figure shows that, for high values of displacement, the gradient of curve 21, which is representative of the force/displacement characteristic of the normal magnet, reaches a higher value than the gradient of curve 23, which is representative of the squeezing characteristic of the elastic tube. The present invention is based on the finding that, when such a normal magnet is used, collapsing and, consequently, a non-continuous squeezing behaviour of the elastic tube can be avoided by using, for the purpose of actuating the squeezing device, an electromagnet 10 having a characteristic whose gradient of the force with respect to the displacement is at each operating point smaller than the gradient of the force with respect to the displacement occurring when the elastic tube 16 is squeezed. For a continuous adjustability of the flow resistance of the valve according to the present invention with a stable operating point, it will be important that the characteristic of the magnet is not steeper than the characteristic of the tube at any operating point, each of said operating points being determined by the drive currents and the armature displacement.

This is preferably guaranteed when the characteristic in question extends comparatively horizontally or descends, such a characteristic being shown by curve 22 in FIG. 3 by way of example. The realization of a desired force/displacement characteristic, which has, for example, the shape of curve 22 in FIG. 3, is unproblematic for persons skilled in the art and is achieved e.g. by providing the pole surfaces 19, 20 of the yoke 14, which define the air gap 15, and the armature 12 with an adequately designed geometry. In view of the elastic properties of the tube 16, a restoring force is generated, which increases as the tube 16 is squeezed to an increasing extent and which acts on the tappet 12a. The armature 12 will squeeze together the tube 16 until an equilibrium has been established between the magnetic force acting on said armature and the restoring force generated by the tube 16. It follows that the inside cross-section of the tube and, consequently, the flow resistance of the valve 4 can be controlled by an appropriate selection of the drive current.

In order to keep the forces which are required for squeezing together the tube as small as possible, the area in which the tube 16 is squeezed together should be as narrow as possible.

In connection with the structural designs of the tappet 12a and of the bearing device 17 shown in FIG. 4, this is achieved on the basis of the fact that the bearing device defines a flat contact surface 17a, whereas the tappet is provided with a convex contact surface 12b at the front end thereof.

As can be seen in FIG. 5, it is just as well possible to provide the contact surface 12b of the tappet 12a with a flat structural design, whereas the contact surface 17a of the bearing device 17 is provided with a convex structural design.

Preferably, the control unit 5 temporarily holds the valve 4 in a partly open condition, when the cuff 1 is being filled, so as to cause a retarded pressure rise of the cuff pressure. The valve 4 is thus used as a controllable bypass.

FIG. 6 includes various pressure rise curves, which occur when a socalled neonatal cuff is filled with a diaphragm pump, so as to elucidate the manner in which the valve of the blood pressure measuring device according to the present invention is controlled as a bypass valve.

The normal case is shown in curve 1, i.e. the valve 4 is closed during inflation. The maximum pressure of 150 mmHg, which must not be exceeded in connection with neonales, will be reached after approx. 250 ms, said time corresponding to 12 to 13 revolutions of the motor of the diaphragm pump.

Curves 2 and 3 show the pressure rises occurring with respect to differently sized opening cross-sections, when the valve is controlled by the control unit 5 in the bypasslike manner described hereinbefore. In comparison with the ascent of curve 1, the ascents of curves 2 and 3 are clearly less steep. Hence, the period of time required will be longer and more revolutions of the motor of the diaphragm pump will be necessary so that a more precise control of the final pressure will be possible.

As has been described hereinbefore, the valve of the blood pressure measuring device according to the present invention permits high discharge rates on the basis of large possible opening cross-sections, an arbitrarily adjustable vent characteristic and, consequently, the use of a single valve for sphygmomanometer sleeves of different volumes, continuous as well as stepwise venting, and a high service reliability in view of the fact that the valve is insensitive to contaminations. The valve has a normally open operating mode and, consequently, it will work reliably if the electricity supply breaks down. The valve consists of a small number of individual components and does not require any precision parts so that it can be manufactured at a reasonable price. On the basis of the continuously adjustable discharge rate, an extension of the opening times with decreasing cuff pressures can be avoided.

I claim:

1. A device for automatically measuring the blood pressure, comprising a sphygmomanometer cuff, a pressure generation device for filling the cuff, a pressure sensor for detecting the cuff pressure, a valve for controllably venting the cuff, said valve comprising an elastic tube and a squeezing device adapted to be actuated by an electromagnet and used for said elastic tube, and a control unit for controlling the valve, wherein said electromagnet has a structural design of such a nature that the gradient of the force with respect to the displacement of its force/displacement characteristic is at each operating point smaller than the gradient of the force with respect to the displacement of the force/displacement characteristic occurring when the elastic tube is squeezed.

2. A device according to claim 1, wherein the electromagnet has a structural design of such a nature that, with a given drive current, the force of said electromagnet is essentially independent of the actuating displacement.

3. A device according to claim 1, wherein the squeezing device comprises a bearing device, which is arranged on one side of the tube, and a tappet actuated by the electromagnet and arranged in such a way that is adapted to be pressed onto the tube on the side of the tube located opposite the bearing device so as to squeeze the tube between the bearing device and the tappet.

4. A device according to claim 3, wherein the bearing device is provided with a convex contact surface for the tube, and the tappet is provided with a flat contact surface for the tube.

5. A device according to claim 3, wherein the bearing device is provided with a flat contact surface for the tube, and the tappet is provided with a convex contact surface for the tube.

6. A device according to claim 1, wherein, when the cuff is being filled, the control unit holds the valve in a partly open condition so as to cause a retarded pressure rise of the cuff pressure during the cuff-filling operation.

7. A device according to claim 2, wherein the squeezing device comprises a bearing device, which is arranged on one side of the tube, and a tappet actuated by the electromagnet and arranged in such a way that is adapted to be pressed onto the tube on the side of the tube located opposite the bearing device so as to squeeze the tube between the bearing device and the tappet.

8. A device for automatically measuring the blood pressure, comprising a sphygmomanometer cuff, a pressure generation device for filling the cuff, a pressure sensor for detecting the cuff pressure, a valve for controllably venting the cuff, said valve comprising an elastic tube and a device for squeezing said elastic tube, a control unit for controlling the valve, and an electromagnet for actuating said squeezing device so that the force gradient with respect to displacement of the squeezing device by the electromagnet is at each displacement operating point smaller than the force gradient with respect to displacement of the elastic tube.

9. A device for automatically measuring the blood pressure, comprising a sphygmomanometer cuff, a pressure generation device for filling the cuff, a pressure sensor for detecting the cuff pressure, a valve for controllably venting the cuff, said valve comprising an elastic tube and a device for squeezing said elastic tube, and a control unit for controlling the valve, the control unit including means for applying non-increasing forces to the tube as it reduces the tube passage cross sectional area.

10. A device for automatically measuring the blood pressure, comprising a sphygmomanometer cuff, a pressure generation device for filling the cuff, a pressure sensor for detecting the cuff pressure, a valve for controllably venting the cuff, said valve comprising an elastic tube and a device for squeezing said elastic tube, and a control unit for controlling the valve, the control unit including means for applying forces to the tube to reduce the tube passage cross sectional area until an equilibrium has been established between the force applied by the squeezing device to the tube and the tube restoring force, the force applying means including an electromagnet having an armature acting on the tube and having non-increasing forces applied to it as it reduces the tube passage cross sectional area.

* * * * *